United States Patent
Vidal Esmoris et al.

(10) Patent No.: US 10,166,178 B2
(45) Date of Patent: Jan. 1, 2019

(54) DEPILATORY WAX COMPOSITION, METHOD FOR OBTAINING SAME AND USE THEREOF

(71) Applicant: GRUPO DRV PHYTOLAB, S.L., Colmenar Viejo (Madrid) (ES)

(72) Inventors: Raúl Vidal Esmoris, Colmenar Viejo (ES); Gema García De Miguel, Colmenar Viejo (ES)

(73) Assignee: GRUPO DRV PHYTOLAB, S.L., Colmenar Viejo (Madrid) (ES)

( * ) Notice: Subject to any disclaimer, the term of this patent is extended or adjusted under 35 U.S.C. 154(b) by 0 days.

(21) Appl. No.: 14/348,985

(22) PCT Filed: Mar. 24, 2014

(86) PCT No.: PCT/ES2014/070221
§ 371 (c)(1),
(2) Date: Oct. 13, 2015

(87) PCT Pub. No.: WO2015/144941
PCT Pub. Date: Oct. 1, 2015

(65) Prior Publication Data
US 2016/0038399 A1   Feb. 11, 2016

(51) Int. Cl.
| | | |
|---|---|---|
| A61K 8/73 | (2006.01) | |
| A61Q 9/04 | (2006.01) | |
| A61K 8/39 | (2006.01) | |
| A61K 8/81 | (2006.01) | |
| A61K 8/92 | (2006.01) | |
| A61K 8/31 | (2006.01) | |

(52) U.S. Cl.
CPC ............... *A61K 8/735* (2013.01); *A61K 8/31* (2013.01); *A61K 8/39* (2013.01); *A61K 8/8111* (2013.01); *A61K 8/922* (2013.01); *A61Q 9/04* (2013.01)

(58) Field of Classification Search
None
See application file for complete search history.

(56) References Cited

U.S. PATENT DOCUMENTS

| 4,282,877 A | * | 8/1981 | Mathews | |
|---|---|---|---|---|
| 2012/0301417 A1 | * | 11/2012 | Pays | A61K 8/8111 424/70.7 |
| 2013/0243706 A1 | * | 9/2013 | Barone | A61K 8/31 424/59 |

FOREIGN PATENT DOCUMENTS

| EP | 0194181 | 9/1985 |
|---|---|---|
| EP | 3009168 | 4/2016 |
| WO | WO 02/085318 | 10/2002 |

OTHER PUBLICATIONS http://www.merriamwebster.com retrieved Jan. 25, 2011.*
International Search Report issued by the International Searching Authority (ISA/O.E.P.M.) dated Nov. 25, 2014 in connection with International Application No. PCT/ES2014/070221.
Extended European Search Report issued by the European Patent Office in connection with European Application No. EP 14887531.3 dated Aug. 1, 2017.
Anonymous: Bulletin 22 HYDRACIRE S—Jojoba Wax, Sunflower Wax & Mimosa Wax, Sep. 15, 2009 (Sep. 15, 2009), URL:http://alliance2u.com/pdf/Bulletin22.pdf.
Gattefosse: "3 Waxes, 3 Benefits, 1 Ingredient acticire" , Apr. 16, 2013 (Apr. 16, 2013), URL:http://www.scsformulate.co.uk/wp-content/uploads/2015/08/Acticire-Brochure.pdf.

* cited by examiner

*Primary Examiner* — James W Rogers
(74) *Attorney, Agent, or Firm* — Gary J. Gershik; Cooper & Dunham LLP

(57) ABSTRACT

The present invention relates to a fat-soluble depilatory wax composition which includes hydrophilic cosmetic active agents adding cosmetic properties to treatment for the purpose for which this composition is used. In other words, the present invention relates to the method for obtaining said composition and to the use thereof for simultaneously depilating and treating skin.

6 Claims, No Drawings

DEPILATORY WAX COMPOSITION, METHOD FOR OBTAINING SAME AND USE THEREOF

RELATED APPLICATIONS

This application is a § 371 national stage of PCT International Application No. PCT/ES2014/070221, filed Mar. 24, 2014, the contents of each of which are hereby incorporated by reference into this application.

OBJECT OF THE INVENTION

The present invention relates to a fat-soluble depilatory wax composition based on colophony resins and/or derivatives thereof and/or hydrocarbon resins and incorporates hydrophilic cosmetic active agents that improve the cosmetic properties of the composition.

It also relates to the method for obtaining said composition and to the use of the composition for simultaneously depilating and treating skin.

BACKGROUND OF THE INVENTION

The main function of depilatory waxes is for them to have adherent properties that facilitate hair removal. Hydrocarbon resins and colophony resins and/or derivatives thereof are among the most widely used adherent compounds; all these compounds are fat-soluble in addition to being hydrophobic.

An issue to be solved in said waxes is the inclusion of water-soluble compounds in fat-soluble depilatory waxes, achieving a stable final composition.

In the state of the art, patent application with publication number WO02/085318 describes the addition of triethanolamine in a colophony resin-based depilatory composition. Furthermore, triethanolamine is an irritant that is aggressive on the skin and does not allow the active ingredients that are carried through same to produce their beneficial effects, therefore regardless of whether its presence allows the inclusion of hydrophilic compounds, the addition thereof to compositions that will be in contact with the skin is neither desirable nor suitable. Furthermore, the percentage of hydrophilic compounds that can be introduced with triethanolamine is low.

Therefore, it can be derived from what is known in the state of the art that there is still a need to develop a fat-soluble depilatory wax composition which, in addition to being able to comprise hydrophilic compounds, is stable, not aggressive on the skin, and includes favorable compounds that are beneficial for the skin.

Until now, the stable incorporation of hydrophilic cosmetic active agents in fat-soluble depilatory wax compositions has been impossible because the medium in which triethanolamine was incorporated experienced a significant change in the pH at which the active ingredients are effective. As a result of the foregoing, there is a need to improve the mechanisms for incorporating said beneficial cosmetic active agents.

DESCRIPTION OF THE INVENTION

Depilatory waxes are used for skin hair removal. In addition to the hair removal function characteristic of depilatory waxes, it would be very desirable to apply together with the wax an agent that is beneficial to the skin and to in turn perform a cosmetic treatment. The present invention is based on the discovery that it is possible to include hydrophilic cosmetic active agents in fat-soluble depilatory compositions and that the composition furthermore remains stable.

These hydrophilic cosmetic active agents have beneficial properties. The actual carrier which introduces the active agents into the depilatory composition also has benefits, such as improved product emollience.

For this purpose, the present invention develops a depilatory composition based on hydrocarbon resins and/or colophony resins and/or derivatives thereof, in which a hydrophilic cosmetic active agent is included.

The depilatory composition comprises a carrier which allows introducing hydrophilic compounds having cosmetic properties and improving the performance of the depilatory composition and its cosmetic activity.

The inclusion of a hydrophilic active agent in a fat-soluble depilatory wax base is achieved with the invention.

Therefore, a first aspect of the invention relates to depilatory wax compositions comprising:
- 60% to 70% by weight of hydrocarbon resins and/or colophony resins, and/or derivatives thereof with respect to the total weight of the composition;
- 1% to 15% by weight of a carrier obtained by the reaction of at least one liquid wax, a solid wax and a polyglycerol or polyglycerol ester with respect to the total weight of the composition;
- 0.01% to 15% by weight of a hydrophilic cosmetic active agent with respect to the total weight of the composition.

In the present invention, "hydrocarbon resins" are understood as synthetic resins derived from petroleum.

In the present invention, "colophony resins" are understood as resins obtained from conifers. The term colophony resins also includes colophony resins that are esterified, modified with a polyhydroxy alcohol such as glycerol or pentaerythritol, for example.

In the present invention, "solid wax" is understood as waxes with a melting point between 50° C. and 90° C. Examples of solid waxes are carnauba wax, candelilla wax, rice wax, sunflower wax, sugarcane wax, beeswax.

In the present invention, "liquid wax" is understood as waxes that are liquid at room temperature or at a temperature between 15° C. and 25° C. Examples of liquid waxes are jojoba wax, lanolins, butters.

The term "hydrophilic cosmetic active agent" means a water-soluble compound from which a cosmetic effect on the skin is derived.

The carrier included in the composition of the invention is the result of the simultaneous reaction between a solid wax, and liquid wax and polyglycerol or polyglycerol ester.

The compositions of the invention have the following advantageous features with respect to the compositions of the state of the art:
- the carrier included in the formula preserves the activity carried out by the active ingredient to be introduced into the final composition of the invention,
- in addition to obtaining depilatory treatment, cosmetic skin treatment is in turn obtained,
- the composition according to the invention has the advantage of being stable despite comprising a significant proportion of hydrophilic compounds,
- in the present invention, good rheological properties are surprisingly obtained with the resulting composition.

Due to the presence of the hydrophilic cosmetic active agents included in the depilatory composition of the invention, the application thereof on the skin allows the action of such products which treat and/or protect the skin. The hydrophilic active agents can provide other concomitant advantages to the depilatory wax, such as anti-aging treatment, hydrating treatment, firming treatment, whitening treatment, revitalizing treatment, mineralizing treatment, restructuring treatment, repairing treatment, exfoliating treatment, a lipolytic effect, a keratolytic effect, a calming effect, and it is painless.

A second aspect of the invention is the method for obtaining the composition comprising the steps of:

a) adding a hydrocarbon resin and/or colophony resins and/or derivatives thereof in a first reactor under stirring at a temperature comprised between 100° C. and 150° C.;

b) adding a mixture of the carrier and the hydrophilic active compound at a temperature comprised between 60° C. and 75° C. in auxiliary equipment under stirring;

c) adding the mixture obtained in the main equipment and keeping the stirring and temperature under control.

DETAILED DESCRIPTION OF THE INVENTION

As mentioned above, the first aspect of the invention relates to a fat-soluble depilatory composition.

In a preferred embodiment, the composition of the invention includes plasticizing agents providing flexibility to the product. In the present invention, the term "plasticizing agent" is understood as a material that is incorporated to provide ductility.

Therefore in one embodiment of the invention, the depilatory composition described in the first aspect of the invention comprises between 5% and 20% of a plasticizing agent.

In a particular embodiment, the composition of the invention includes emollients, thickeners, preservatives and dyes.

In a particular embodiment, the agent of inclusion is an esterification of a mixture of natural waxes selected from mimosa wax, candelilla wax, rice wax, sunflower wax. The liquid wax is preferably jojoba wax. In addition to allowing the introduction of the hydrophilic active agents, this set of waxes has a very significant moisturizing effect. More particularly, the carrier is obtained by the reaction of liquid jojoba wax and solid waxes; mimosa wax and sunflower wax and polyglycerol-3 esters.

Examples of "hydrophilic cosmetic active agents" are the compounds of the human extracellular matrix, for example, collagen fibers; elastin fibers; glycosaminoglycans such as hyaluronic acid, chondroitin-4-sulfate, chondroitin-6-sulfate, dermatan sulfate, heparan sulfate, keratan sulfate; proteoglycans; adhesive glycoproteins such as fibronectin, laminin, entactin, tenascin, chondronectin. Other cosmetic active agents such as natural moisturizing factor and DNA sodium salt of marine origin can also be incorporated.

Finally, a third aspect of the invention is the cosmetic use of the composition of the invention described in the preceding paragraphs for simultaneously depilating and treating skin.

EXAMPLES

Example 1

A reactor was programmed at a temperature comprised between 120° C. and 125° C. The reactor has stirring means, a turbine and a heater.

Paraffins and microcrystalline waxes were added to the reactor, maintaining the temperature between 120° C. and 125° C. Stirring was started and the mixture was allowed to again reach the set temperature of 120° C.-125° C.

The temperature was maintained at 120° C.-125° C. and a hydrocarbon resin was added little by little under stirring to prevent a temperature drop and solid mass formation at the bottom of the reactor.

The plasticizers were added, once the ingredients were melted and mixed, and maintaining the temperature and stirring.

The dyes were added. The activated turbine was maintained until all the components are completely dispersed.

Hyaluronic acid and the lipophilic agent of inclusion obtained by the reaction of liquid jojoba wax and solid waxes; mimosa wax and sunflower wax of the Acticire brand name marketed by Gattefosse under CAS number 68953-55-9, are added in another vessel, maintaining the temperature below 75° C. Once they were melted and mixed completely, after about three and a half to four hours, they were added to the main reactor.

Example 2

A mixture comprising the following is prepared:

| Compound | Function | Percentage |
|---|---|---|
| Polyhydrogenated $C_{6-20}$ olefin | Hydrocarbon resin | 66.4 |
| Paraffin | Base, emollient | 14.0 |
| Microcrystalline wax | Thickener | 7.37 |
| Ethylene/vinyl acetate copolymer | Plasticizer | 6.23 |
| Vinyl acetate | Plasticizer | 4.53 |
| Pentaerythrityl tetra-di-t-butyl hydroxyhydrocinnamate | Preservative | 0.61 |
| Bis(2,2,6,6-tetramethyl-4-piperidyl)sebacate | Preservative | 0.61 |
| Propylene glycol | Preservative | 0.12 |
| Water | Solvent | 0.09 |
| Mimosa/jojoba/sunflower waxes and polyglycerol-3 esters | Carrier | 0.05 |
| Violet 2 CI60725 | Dye | 0.0040 |
| Sodium hyaluronate | Active ingredient | 0.0038 |
| Mica | Dye | 0.0009 |
| Titanium dioxide CI77891 | Dye | 0.0004 |

The invention claimed is:

1. A depilatory composition consisting of:
   60% to 70% by weight with respect to the total weight of the composition of synthetic resins selected from the group consisting of petroleum resin and colophony resin;
   1% to 15% by weight with respect to the total weight of the composition of a carrier;
   0.01% to 15% by weight with respect to the total weight of the composition of a hydrophilic cosmetic active agent,
   wherein the carrier introduces the active agent into the depilatory composition, and wherein the carrier is obtained by reaction of liquid jojoba wax, mimosa wax and sunflower wax with polyglycerol-3 esters.

2. The composition according to claim 1, wherein the hydrophilic cosmetic active agent is a component of the human extracellular matrix.

3. The composition according to claim 1, wherein the cosmetic active agent is hyaluronic acid.

4. A method for simultaneously depilating and treating skin comprising applying the composition of claim 1 to the skin to be treated thereby depilating and treating the skin.

5. A method for simultaneously depilating and treating skin comprising applying the composition of claim 2 to the skin to be treated thereby depilating and treating the skin.

6. A method for simultaneously depilating and treating skin comprising applying the composition of claim 3 to the skin to be treated thereby depilating and treating the skin.

\* \* \* \* \*